(12) United States Patent
Gupta et al.

(10) Patent No.: US 6,996,952 B2
(45) Date of Patent: Feb. 14, 2006

(54) METHOD FOR IMPROVING STABILITY AND EFFECTIVITY OF A DRUG-DEVICE COMBINATION PRODUCT

(75) Inventors: Rainuka Gupta, Cambridge, MA (US); Alan J. Dextradeur, Franklin, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 167 days.

(21) Appl. No.: 10/676,333

(22) Filed: Sep. 30, 2003

(65) Prior Publication Data

US 2005/0067312 A1    Mar. 31, 2005

(51) Int. Cl.
*B65B 31/06*    (2006.01)
*B65B 55/18*    (2006.01)

(52) U.S. Cl. ............................ 53/434; 53/449; 53/469; 53/425

(58) Field of Classification Search .................. 53/434, 53/512

See application file for complete search history.

(56) References Cited

U.S. PATENT DOCUMENTS

| | | | |
|---|---|---|---|
| 3,726,057 A | | 4/1973 | Kemble |
| 3,761,013 A | * | 9/1973 | Schuster ..................... 206/439 |
| 3,815,315 A | * | 6/1974 | Glick .......................... 53/425 |
| 3,939,971 A | * | 2/1976 | Tulis .......................... 206/205 |
| 4,603,538 A | | 8/1986 | Shave |
| 4,644,586 A | | 2/1987 | Padgett |
| 4,683,702 A | * | 8/1987 | Vis .............................. 53/433 |
| 4,709,819 A | | 12/1987 | Lattuada et al. |
| 4,756,140 A | | 7/1988 | Gannon |
| 4,813,210 A | | 3/1989 | Masuda et al. |
| 4,941,308 A | | 7/1990 | Grabenkort et al. |
| 4,949,529 A | | 8/1990 | Davis |
| 5,014,494 A | | 5/1991 | George |
| 5,097,859 A | | 3/1992 | Grabenkort et al. |
| 5,103,618 A | | 4/1992 | Garwood |
| 5,111,836 A | | 5/1992 | Grabenkort |
| 5,143,617 A | | 9/1992 | Grabenkort |
| 5,178,267 A | | 1/1993 | Grabenkort et al. |
| 5,354,569 A | | 10/1994 | Brown et al. |
| 5,577,368 A | | 11/1996 | Hamilton et al. |
| 5,578,075 A | | 11/1996 | Dayton |
| 5,624,704 A | | 4/1997 | Darouiche |
| 5,667,827 A | * | 9/1997 | Breen et al. ................. 426/129 |
| 5,879,620 A | | 3/1999 | Cohen |
| 5,902,283 A | | 5/1999 | Darouiche et al. |
| 6,161,695 A | | 12/2000 | Nicolais |

(Continued)

OTHER PUBLICATIONS

Dawson, L. Paul., "Active Packaging—Coatings and Films for Extending Shelf-Life", Busines Briefing Foodtech (1989).

(Continued)

*Primary Examiner*—John Sipos

(57) ABSTRACT

A package for a drug-device combination product includes an outer package including a first gas impermeable sheet and a second gas impermeable sheet hermetically sealed there to on three sides. A gas permeable header is attached to an unsealed side of the first sheet and sealed to the second sheet on two sides. The first and second gas impermeable sheets and the header form an interior and an opening communicating with the interior. A gas permeable inner package is disposed within the outer package. A product is sealed within the inner package. The inner package is placed within the outer package and a top end of the header is sealed to the second sheet. The outer package is then sealed by sealing the first gas impermeable sheet to the second gas impermeable sheet at a seal point below the point where the header attaches to the first sheet.

14 Claims, 8 Drawing Sheets

U.S. PATENT DOCUMENTS

| | | |
|---|---|---|
| 6,174,934 B1 | 1/2001 | Sun et al. |
| 2002/0062147 A1* | 5/2002 | Yang ........................ 623/1.13 |
| 2002/0082679 A1* | 6/2002 | Sirhan et al. .............. 623/1.15 |
| 2003/0033007 A1* | 2/2003 | Sirhan et al. .............. 623/1.42 |
| 2003/0050692 A1* | 3/2003 | Sirhan et al. .............. 623/1.42 |
| 2003/0083646 A1* | 5/2003 | Sirhan et al. ............ 604/891.1 |
| 2003/0139801 A1* | 7/2003 | Sirhan et al. .............. 623/1.15 |

OTHER PUBLICATIONS

Tolas Products, "Dispose-A-Vent", http://www.tolas.com/disposavent.htm.

* cited by examiner

METHOD FOR IMPROVING STABILITY AND EFFECTIVITY OF A DRUG-DEVICE COMBINATION PRODUCT

BACKGROUND OF THE INVENTION

1. Field of the Invention

This invention relates to a package for a drug-device combination product having an outer package including a first gas impermeable sheet, a second gas impermeable sheet and a gas permeable header.

2. Discussion of the Related Art

Packaging a product in an inner package and then packing the inner package in an outer package is common in the packaging arts. Vacuum packaging, packaging with an inert gas and multiple methods of sterilizing medical products are known in the medical device packaging art. However, drug-device combination products offer a new and unique problem in the packaging and sterilizing of the product, while refraining from altering the chemical structure of the drug incorporated in the device.

Numerous inventions relate to the use of radiation to sterilize products for medical use, for example, U.S. Pat. No. 5,577,368 to Hamilton et al. ("Hamilton") and U.S. Pat. No. 6,174,934 to Sun et al. ("Sun"). Both Hamilton and Sun first remove the oxygen/atmosphere from the packaging prior to radiation sterilizing medical implants made of polymeric material. Hamilton's and Sun's goal is to reduce the wear resistance of the polymeric implant and, radiation typically alters the chemical structures of incorporated drugs.

Other inventions known in the art require numerous complex steps to sterilize and seal a medical device in one or more packages. U.S. Pat. No. 4,709,819 to Lattuada et al. discloses first sterilizing an outer package, placing an inner package in the outer package and then evacuating both the inner and outer packages. This process is used because Lattuada et al. are packaging biological samples and any sterilization of the inner package would kill the sample.

Further, U.S. Pat. No. 4,941,308 to Grabenkort et al. discloses sterilizing the interior of the package before placing the product in the inner package, sterilizing the product in the inner package, and then placing the inner package in the outer package. Additionally, Grabenkort et al. uses ethylene oxide gas (EtO) for the sterilization.

Both Lattunda et al. and Grabenkort et al. require a separate sterilizing step prior to inserting and sealing the inner package in the outer package. This adds steps and cost to the handling of the already sterilized product/inner package prior to inserting it into the outer package.

Thus, there is a need in the art for a packaging product and method to sterilize a drug-incorporated device in the minimum number of steps while refraining from altering the chemical structure of the drug incorporated in the device.

SUMMARY OF THE INVENTION

A package for a drug-device combination product includes an outer package, including a first gas impermeable sheet and a second gas impermeable sheet hermetically sealed on three sides. The impermeable sheet material should be flexible and can be selected from among many types of high barrier, flexible packaging materials that are commonly used to enclose medical devices. Preferably the impermeable sheet material is a multilayered, heat seal peelable packaging material that includes one or more foil layers, various polymer layers and a heat seal coating. Examples of suitable materials are those that include the following layers: polyester film-low density polyethylene-foil-ionomer-heat seal coating. Packaging materials having the following layers can also be used: polyester-low density polyethylene-foil-EAA-linear low density polyethylene-heat seal coating; and polyester-Surlyn-nylon-Surlyn-foil-EAA-linear low density polyethylene-heat seal coating. Additionally, polyvinylidene chloride (PVDC) and ethylene vinyl alcohol copolymer, (EVOH), are genrally key components of a high-barrier film. Nylons, acrylonitrile methacrylate copolymer (AN-MA), and other specialty polymers such as certain copolyesters may potentially be used.

A gas permeable header is attached to an unsealed side of the first gas impermeable sheet and sealed to the second gas impermeable sheet on two sides. The first and second gas impermeable sheets and the gas permeable header form an interior and an opening that communicates with the interior to form three sealed sides of the outer package.

A gas permeable inner package is sized to fit the device and disposed within the outer package and preferable disposed only between the first and second gas impermeable sheets. The gas permeable material for both the header and/or the inner package can be Tyvek® or any other durable gas permeable material such as polyethylene, polystyrene or polypropylene. The gas permeable inner package can be a blister tray, a pouch, or any other gas permeable container designed to hold a product to be sterilized. The product can be incorporated with drugs that are antimicrobial agents, antiangiogenesis, antiproliferatives, and anti-inflammatorys. Incorporating the drug into the product can include, but is not limited to, impregnating, coating and sandwiching the drug between layers of the device.

In an embodiment of the product, the antimicrobial agent can be selected from the group comprising antibiotics, antiseptics, and disinfectants. Further, the antibiotics can be selected from a group comprising tetracyclines (i.e. minoclcine), penicillins, (i.e. nafcillin), macrolides (i.e. erythromycin), rifampin, gentamicin, vancomycinclindamycin, azithromycin, enoxacin, and combinations thereof. A preferred product is incorporated with Rifampicin or Clindamycin.

Antiangiogenesis drugs (also called angiogenesis inhibitors) deprive the cancer cells of their blood supply. Antiangiogenesis can be selected from the group including angiostatin, thalidomide (Thalomid™), CC-5013 (Revimid™), bevacizumab (Avastin™), squalamine, endostatin, angiostatin, and angiozyme. Other antiangiogenesis drugs can include drugs derived from chemotherapy drugs, for example, paclitaxel (Taxol™), doxorubicin (Adriamycin™), epirubicin, mitoxantrone, and cyclophosphamide.

Antiproliferative drugs can prevent restenosis (a re-narrowing or blockage of an artery at the same site where treatment, such as an angioplasty or stent procedure, has already taken place) of the implanted device. Examples of antiproliferatives are Sirolimus™ and Paclitaxel™. Examples of anti-inflammatories, including non-steroidal anti-inflammatory drugs (NSAID's), are ibuprofen, ketoprofen, motrin, and naproxen.

Once the product is sealed within the inner package, the inner package is placed within the outer package and a top end of the header is sealed to the second sheet. This forms a sealed outer package that has gas permeable and impermeable sections. Up to this point, only minimal care is required, neither the product, inner package, nor outer package has been sterilized and special handling or handling in a clean environment is not required. However, a preferred embodiment includes handling in a clean room environment to minimize the introduction of contaminants.

The sterilizing compound is then introduced into the interior of the outer package through the header. Since the inner package is also permeable, the sterilizing compound can permeate through the inner package and sterilize the product. As above, the sterilizing compound can be steam, ethylene oxide gas (EtO), gas plasma/radio frequency-peroxide (e.g. Sterrad™), chemical vapor (e.g alcohol, formaldehyde, etc), and cold sterilization using liquid chemical sterilants/disinfectants that require immersion (e.g. glutaraldehyde and chlorine dioxide). The invention allows for any sterilization process that utilizes a sterilizing agent that can only pass through a permeable layer.

Once the product is sterilized, the atmosphere can be evacuated from the interior to 'vacuum seal' the product, as well as retard further oxidation. The outer package is then sealed by sealing the first gas impermeable sheet to the second gas impermeable sheet at a seal point below the point where the header attaches to the first sheet. The outer package is now a gas impermeable package. The header can either be removed or folded over to complete the packaging.

A key feature of the sterilizing step includes using any sterilizing process that maintains a chemical structure of the drug as well as prevents oxidation of the drug, and still sterilizes the product for medical use.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein.

Figure 4:
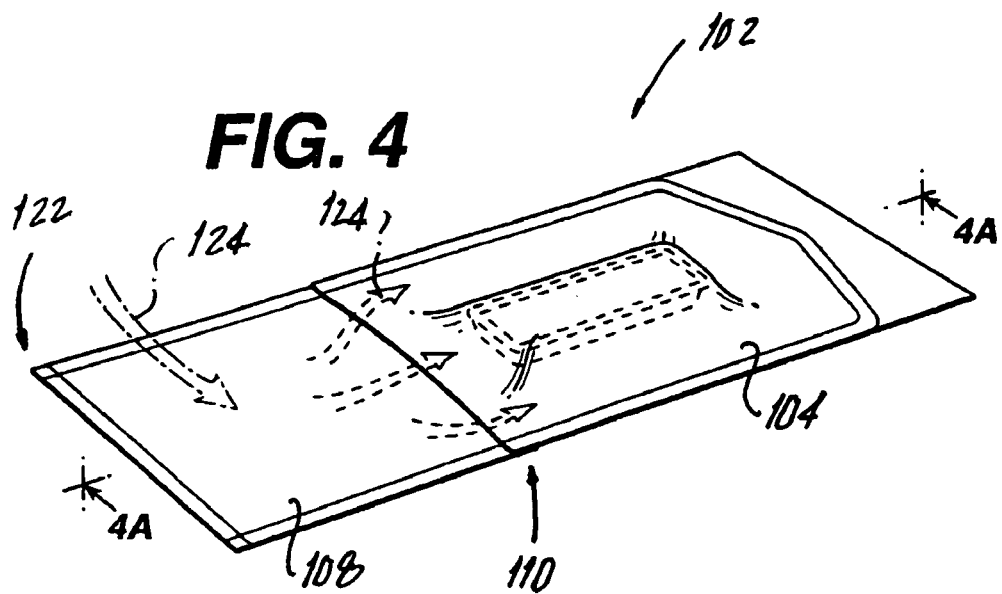
Figure 4A:
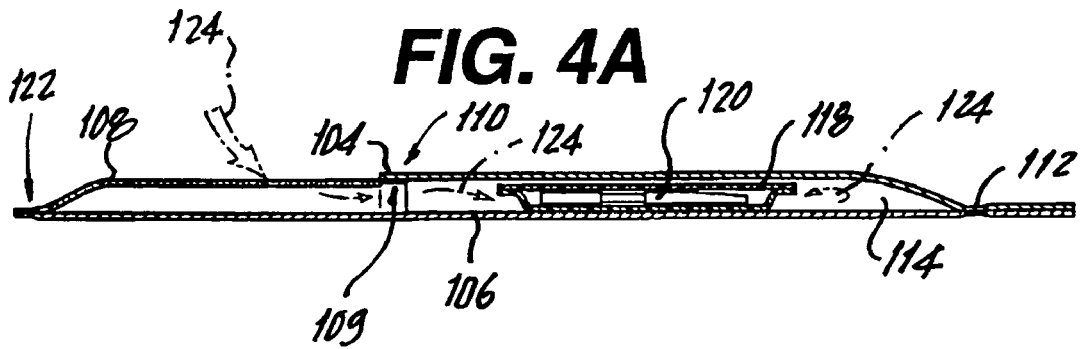
Figure 5:
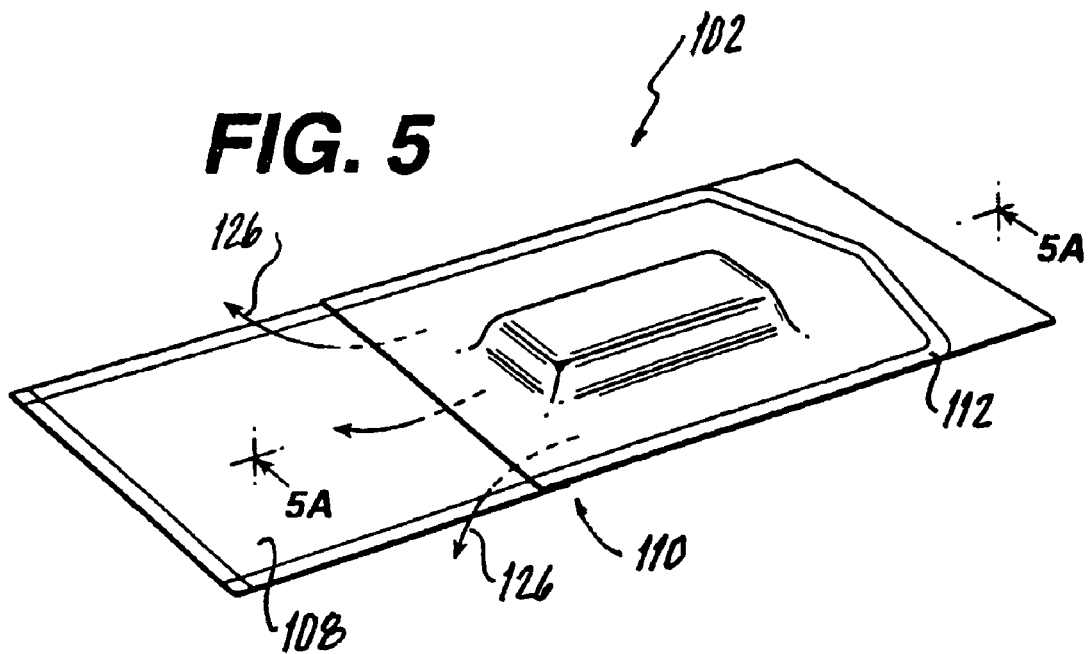
Figure 5A:
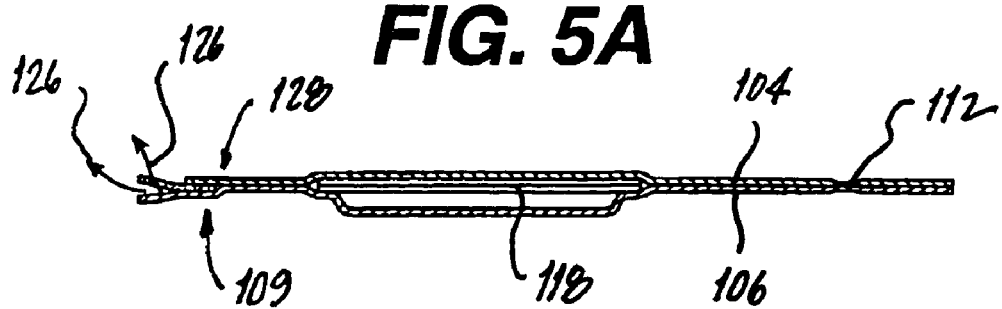
Figure 6:
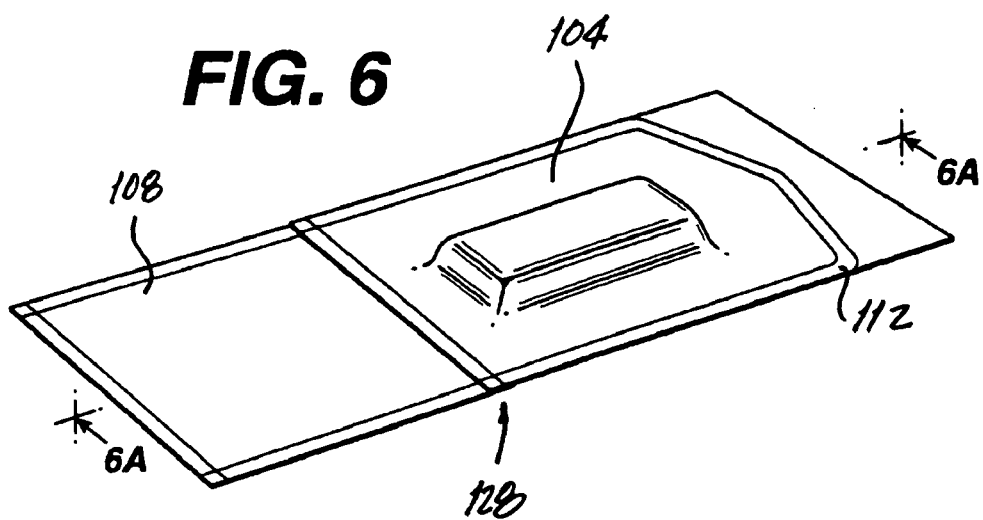
Figure 6A:
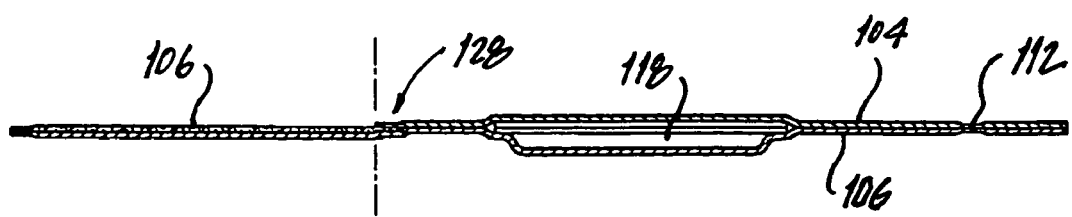
Figure 7:
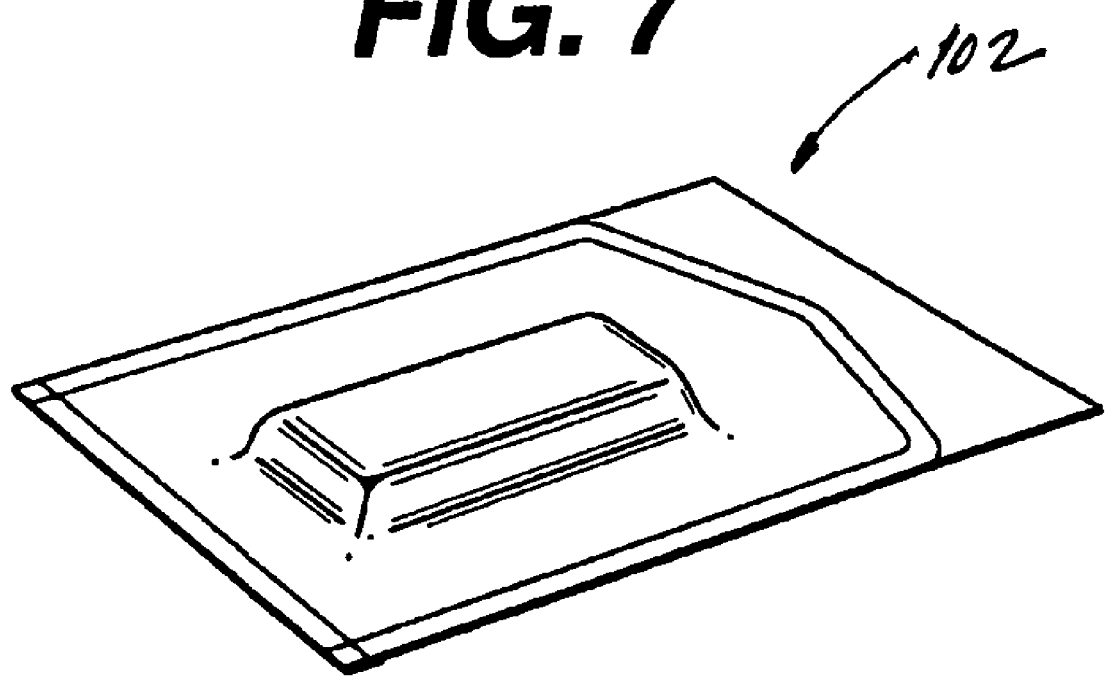

FIG. 4 a perspective view of the of the inner package and outer package during sterilization;

FIG. 4A is a cross-sectional view along line 4A—4A of FIG. 4;

FIG. 5 is a perspective view of the inner package and outer package during evacuation;

FIG. 5A is a cross-sectional view along line 5A—5A of FIG. 5;

FIG. 6 is a perspective view of the inner package and outer package after evacuation;

FIG. 6A is a cross-sectional view along line 6A—6A of FIG. 6;

FIG. 7 is a perspective view of the final packaging; and

Figure 8:
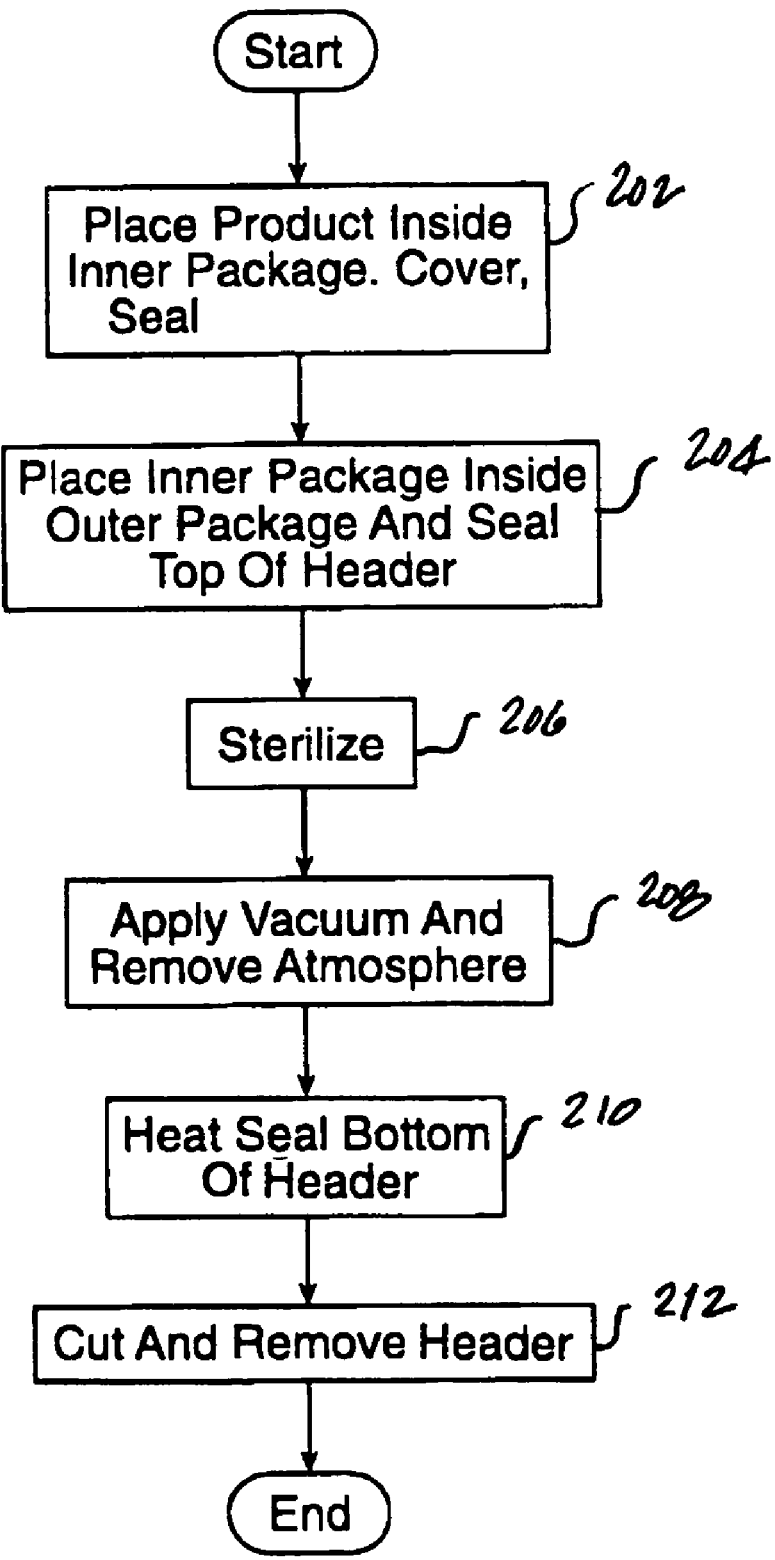

FIG. 8 is a flow chart outlining the method of the present invention.

DETAILED DESCRIPTION OF THE PREFERRED EMBODIMENT

Figure 1:
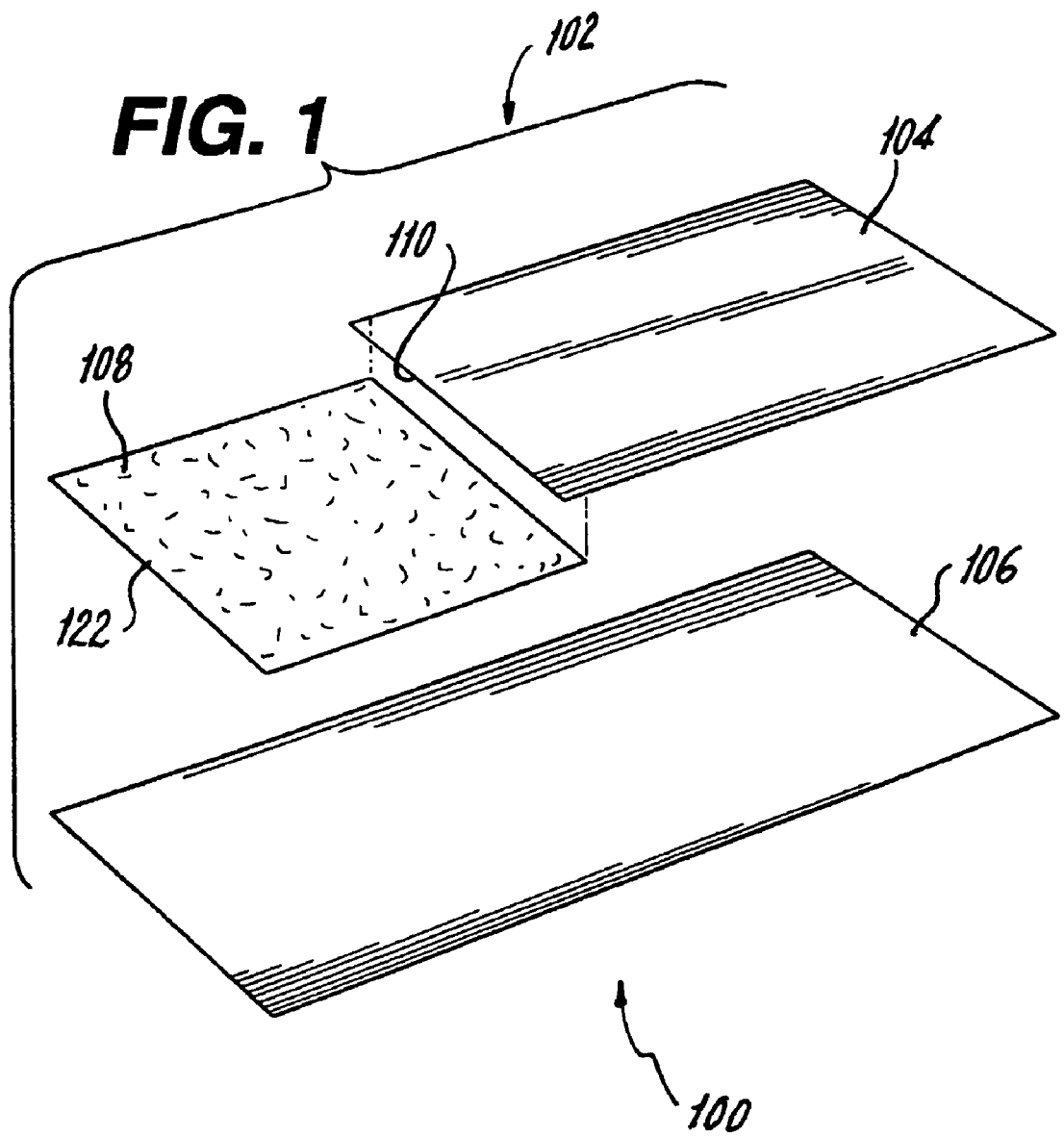
FIG. 1 is an exploded perspective view of the outer package of the present invention.
Figure 2:
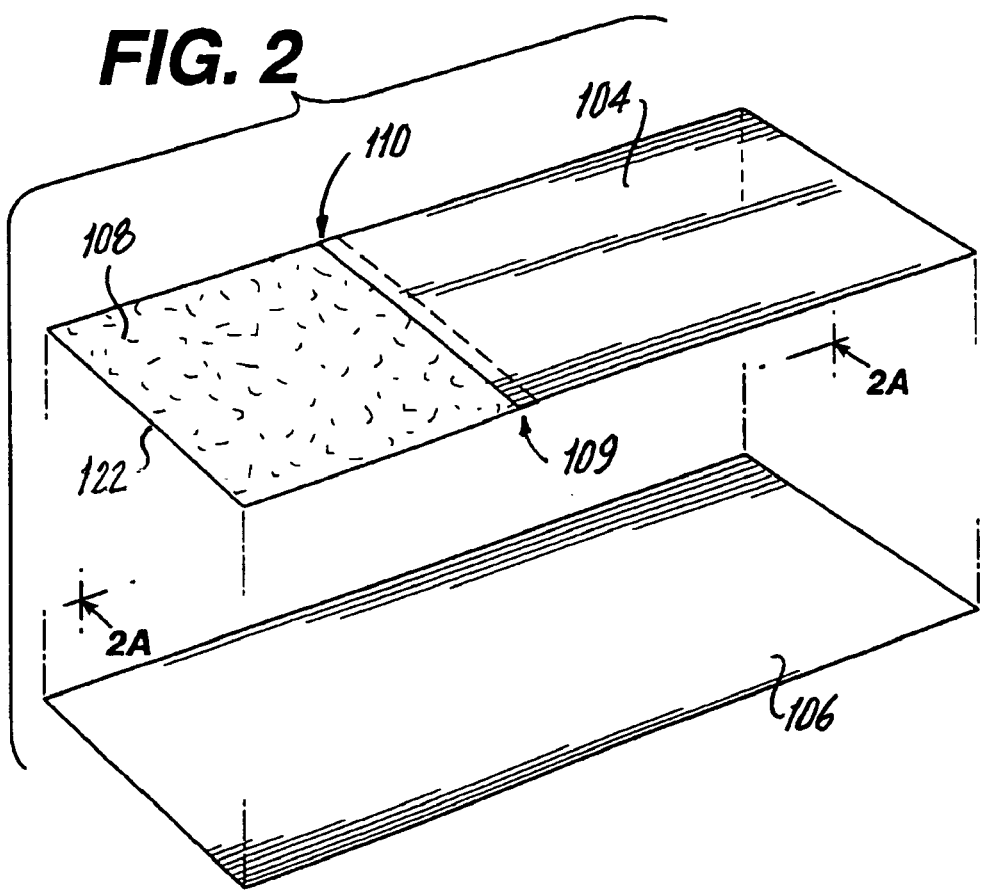
FIG. 2 is a perspective view of the outer package of the present invention.
Figure 2A:
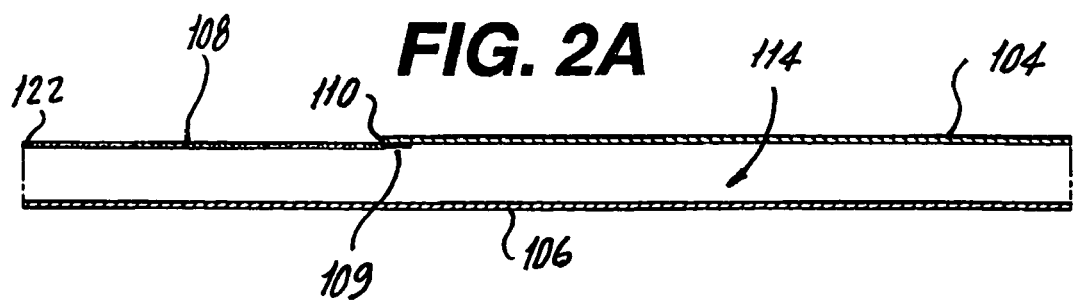
FIG. 2A is a cross-sectional view along line 2A—2A of FIG. 2.
Figure 3:
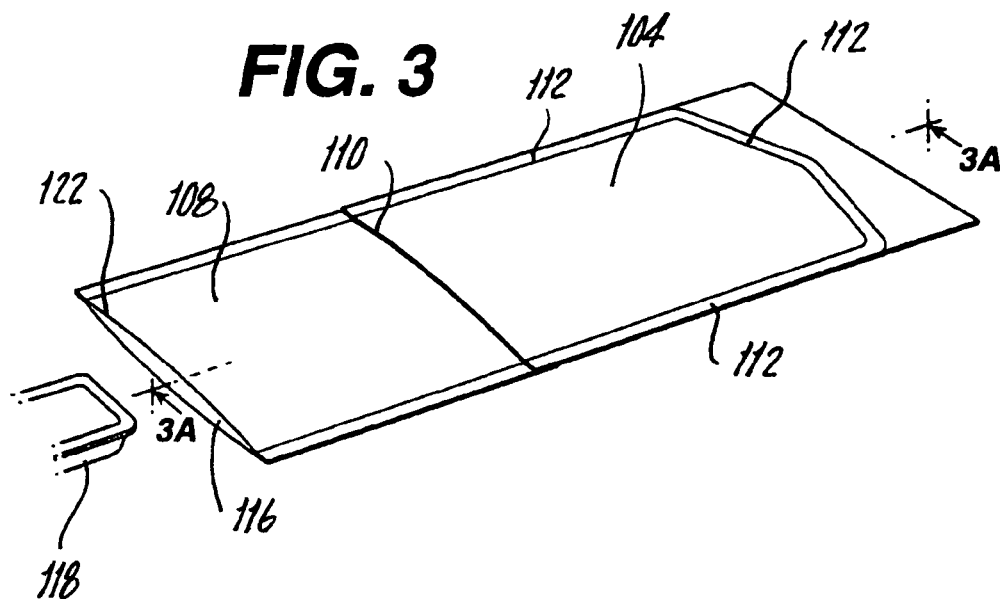
FIG. 3 is a perspective view of the of the assembled outer package prior to the insertion of the inner package.
Figure 3A:
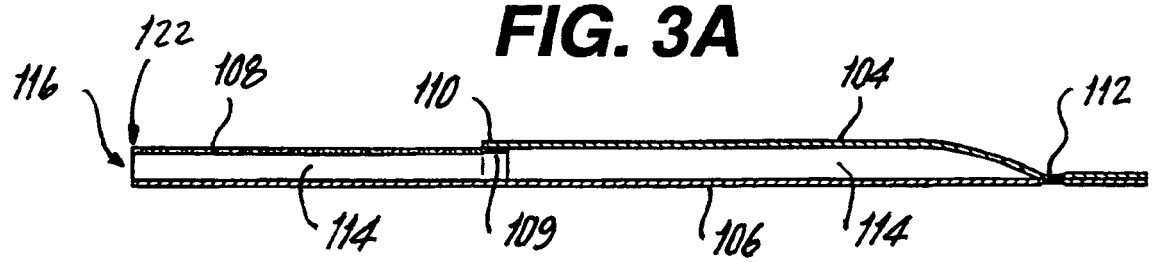
FIG. 3A is a cross-sectional view along line 3A—3A of FIG. 3.

Referring now to FIGS. 1 through 3A, a package 100 for a drug-device combination product is illustrated. Package 100 includes an outer package 102 including a first gas impermeable sheet 104 and a second gas impermeable sheet 106 hermetically sealed on three sides 112 (FIG. 3). A gas permeable header 108 is attached at an attachment point 109 located on an unsealed side 110 of first gas impermeable sheet 104 and sealed to second gas impermeable sheet 106 on two sides. First and second gas impermeable sheets 104, 106 and gas permeable header 108 form an interior 114 with an opening 116 communicating with interior 114. The impermeable sheet material should be flexible and can be selected from among many types of high barrier, flexible packaging materials that are commonly used to enclose medical devices. Preferably the impermeable sheet material is a multilayered, heat seal peelable packaging material that includes one or more foil layers, various polymer layers and a heat seal coating. Examples of suitable materials are those that include the following layers: polyester film-low density polyethylene-foil-ionomer-heat seal coating. Packaging materials having the following layers can also be used: polyester-low density polyethylene-foil-EAA-linear low density polyethylene-heat seal coating; and polyester-Surlyn-nylon-Surlyn-foil-EAA-linear low density polyethylene-heat seal coating. Additionally, polyvinylidene chloride (PVDC) and ethylene vinyl alcohol copolymer, (EVOH), are genrally key components of a high-barrier film. Nylons, acrylonitrile methacrylate copolymer (AN-MA), and other specialty polymers such as certain copolyesters may potentially be used.

Referring to FIGS. 3 through 4A, a gas permeable inner package 118 is disposed within outer package 102. Additionally, gas permeable inner package 118 is preferably disposed only between first and second gas impermeable sheets 104, 106. The gas permeable material for both the header and/or the inner package can be Tyvek® or any other durable gas permeable material such as polyethylene, polystyrene or polypropylene. Gas permeable inner package 118 can be a blister tray, a pouch, or any other gas permeable container designed to hold a product 120 to be sterilized.

FIG. 4A illustrates product 120 which, in an embodiment, can be incorporated with a drug (not illustrated) and gas permeable inner package 118 is sized to contain product 120 and be placed only between gas impermeable section of first sheet and second sheet 104, 106. The drugs that the product can be incorporated with are antimicrobial agents, antiangiogenesis, antiproliferatives, and anti-inflammatorys. Incorporating the drug into the product can include, but is not limited to, impregnating, coating and sandwiching the drug between layers of product 120.

In an embodiment of product 120, the antimicrobial agent can be selected from the group comprising antibiotics, antiseptics, and disinfectants. Further, the antibiotics can be selected from a group comprising tetracyclines (i.e. Minoclcine™), penicillins, (i.e. Nafcillin™), macrolides (i.e. Erythromycin™), rifampin, gentamicin, vancomycinclindamycin, azithromycin, enoxacin, and combinations thereof. A preferred product 120 is incorporated with Rifampicin™ or Clindamycin™.

Antiangiogenesis drugs (also called angiogenesis inhibitors) deprive the cancer cells of their blood supply. Antiangiogenesis can be selected from the group including angiostatin, thalidomide (Thalomid™), CC-5013 (Revimid™), bevacizumab (Avastin™), squalamine, endostatin, angiostatin, and angiozyme. Other antiangiogenesis drugs can include drugs derived from chemotherapy drugs, for example, paclitaxel (Taxol™), doxorubicin (Adriamycin™), epirubicin, mitoxantrone, and cyclophosphamide.

Antiproliferative drugs can prevent restenosis (a re-narrowing or blockage of an artery at the same site where treatment, such as an angioplasty or a stent procedure, has already taken place) of product 120. Examples of antiproliferatives are Sirolimus™ and Paclitaxel™. Examples of anti-inflammatories, including non-steroidal anti-inflammatory drugs (NSAID's), are ibuprofen, ketoprofen, motrin, and naproxen.

FIGS. 3 through 4A further illustrate that once product 120 is sealed within inner package 118, inner package 118 is placed within outer package 102. A top end 122 of header 108 is sealed to second sheet 106. A sterilizing compound 124 is then introduced into interior 114 through header 108. Sterilizing compound 124 then permeates through inner package 118 and sterilizes product 120. Sterilizing compound 124 can be steam, ethylene oxide gas (EtO), gas plasma/radio frequency-peroxide (e.g. Sterrad™), chemical vapor (e.g alcohol, formaldehyde, etc), and cold sterilization using liquid chemical sterilants/disinfectants that require immersion (e.g. glutaraldehyde and chlorine dioxide). The invention allows for any sterilization process that utilizes a sterilizing agent that can only pass through a permeable layer and that process is compatible with the incorporated drug. For example, Rifampicin is not compatible with EtO sterilization, but is compatible with steam sterilization.

Referring to FIGS. 5 and 5A, optionally, atmosphere 126 can be evacuated from interior 114 to 'vacuum seal' product 120. Outer package 102 is then sealed by sealing first gas impermeable sheet 104 to second gas impermeable sheet 106 at a seal point 128 below attachment point 109 of header 108 to first sheet 104. Outer package 102 is now a gas impermeable package. Optionally, header 108 can either be removed or folded over to complete the packaging (FIG. 7).

FIG. 8 illustrates a method of packaging a drug-device combination product 120 such as, for example, but not limited to a drug incorporated catheter (e.g. Bactiseal™) and a drug-eluting stent (e.g. Cypher™). The steps include placing product 120 inside gas permeable inner package 118 (step 202), sealing inner package 118, and placing inner package 118 inside outer package 102 (step 204). Outer package 102 is formed as described above. Further steps include sealing the top end 122 of header 108 to second sheet 106 to seal inner package 118 in outer package 102 (step 204). Once inner package 118 is sealed, product 120 is sterilized with sterilizing compound 126 (step 206) and the first sheet 104 is sealed to second sheet 106 to seal inner package 118 in a gas impermeable outer package (step 210). An embodiment includes, after the sterilizing step (206), removing atmosphere 126 from inside outer package 102 (step 208). Once the gas impermeable outer package is sealed, another step includes removing the gas permeable header 108 (step 212), or as an alternative header 108 can be folded under outer package 102.

An embodiment includes, replacing atmosphere 126 with an inert gas (not illustrated) prior to removing the atmosphere 128 (step 208). Another embodiment includes, after removing the atmosphere (step 208), filling the outer package 102 with an inert gas (not illustrated).

A key feature of the sterilizing step includes using steam, EtO, gas plasma/radio frequency-peroxide, chemical vapor, cold sterilization or any sterilizing process that maintains the chemical structure of the incorporated drug, prevents oxidation of the incorporated drug and also maintains the desired mechanical properties (rigidity, elasticity, etc.) of the device, while still sterilizing the product for medical use.

While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

We claim:

1. The method of packaging a drug-device combination product, comprising:
   placing the product inside a gas permeable inner package;
   sealing the inner package;
   placing the inner package inside an outer package, wherein the outer package comprises a first gas impermeable sheet and a second gas impermeable sheet having four sides and hermetically sealed to each other on three sides and a gas permeable header disposed at an unsealed fourth side of the first gas impermeable sheet and sealed to the second gas impermeable sheet on two sides;
   sealing an end of the header to the second sheet to seal the inner package in the outer package;
   sterilizing the product; and
   sealing the first sheet to the second sheet at their fourth sides to seal the inner package in a gas impermeable outer package.

2. The method of claim 1, further comprising, after the sterilizing step, removing an atmosphere inside the outer package.

3. The method of claim 2, further comprising, after the removing step, filling the outer package with an inert gas.

4. The method of claim 2, further comprising, prior to the removing step, filling the outer package with an inert gas.

5. The method of claim 1, further comprising, removing the gas permeable header.

6. The method of claim 1, wherein the sterilizing step comprises at least one of steam sterilization, EtO sterilization, gas plasma/radio frequency-peroxide sterilization, chemical vapor sterilization, and cold sterilization.

7. The method of claim 1, wherein the product is incorporated with at least one of an antimicrobial agent, an antiangiogenes, and antiproliferative, and an anti-inflammatory.

8. The method of packaging a product, comprising:
   placing a combination drug device product inside a gas permeable inner package;
   sealing the inner package;
   placing the inner package inside an outer package, wherein the outer package comprises a first sheet comprising a gas impermeable section, having four sides a gas permeable header disposed at a first side of the gas impermeable section, a second sheet having four sides and being gas impermeable which is hermetically sealed on the other three sides to the first sheet; and on two sides to the gas permeable header
   sealing the header to the second sheet to seal the inner package in the outer package;
   sterilizing the product; and sealing the first sheet to the second sheet at the fourth sides to seal the inner package in a gas impermeable outer package.

9. The method of claim 8, further comprising, after the sterilizing step, removing the atmosphere inside the outer package.

10. The method of claim 9, further comprising, prior to the removing step, filling the outer package with an inert gas.

11. The method of claim 9, further comprising, after the removing step, filling the outer package with an inert gas.

12. The method of claim 8, further comprising removing the gas permeable header.

13. The method of claim 8, wherein the sterilizing step comprises at least one of steam sterilization, EtO sterilization, gas plasma/radio frequency-peroxide sterilization, chemical vapor sterilization, and cold sterilization.

14. The method of claim 8, wherein the product is incorporated with at least one of an antimicrobial agent, an antiangiogenes, and antiproliferative, and an anti-inflammatory.

* * * * *